| United States Patent [19] | [11] Patent Number: 4,760,154 |
| Chang et al. | [45] Date of Patent: Jul. 26, 1988 |

[54] SYNTHESIS OF DIOXANE

[75] Inventors: Clarence D. Chang, Princeton; Stuart D. Hellring, Trenton, both of N.J.

[73] Assignee: Mobil Oil Corporation, New York, N.Y.

[21] Appl. No.: 789,607

[22] Filed: Oct. 21, 1985

[51] Int. Cl.$^4$ .......................................... C07D 319/12
[52] U.S. Cl. .................................................. 549/377
[58] Field of Search ...................................... 549/377

[56] References Cited

FOREIGN PATENT DOCUMENTS

| 540278 | 4/1957 | Canada | 549/377 |
| 49-16433 | 4/1974 | Japan | 549/377 |
| 49-16434 | 4/1974 | Japan | 549/377 |

OTHER PUBLICATIONS

API abstract—Japanese publication, Abstract of J 62070-369-A, (3/31/87).

Primary Examiner—Nicky Chan
Attorney, Agent, or Firm—Alexander J. McKillop; Michael G. Gilman; Marina V. Schneller

[57] ABSTRACT

A catalyzed conversion of diethylene glycol to 1,4-dioxane, undertaken over zeolites, ZSM-5, ZSM-23, ZSM-48 and zeolite beta, is characterized by high selectivity.

13 Claims, No Drawings

SYNTHESIS OF DIOXANE

FIELD OF THE INVENTION

The invention is directed to the catalytic synthesis of dioxane. In particular, diethylene glycol is converted to dioxane.

BACKGROUND OF THE INVENTION

Dioxane is an important industrial solvent for cellulose esters and ethers, and other oils and resins. Sometimes referred to as para-dioxane, 1.4-dioxane, can be produced from the less valuable reactant, diethylene glycol; diethylene is a by-product of ethylene glycol synthesis.

Preparation of dioxane from diethylene glycol by intramolecular cyclization has been catalyzed by adding acid to the reaction to cyclize diethylene glycol. Cf. Weissermel, K.; Arpe, H.-J. "Industrial Organic Chemistry" 1978, Verlag Chemie, New York, pp. 137–138). However, use of such acid catalysts under homogeneous conditions leads to competing intermolecular polymerization. For this reason, the preparation is often done via the corresponding chlorinated species.

DESCRIPTION OF THE INVENTION

In accordance with the invention, diethylene glycol, a by-product of ethylene glycol synthesis, is converted to the commercial solvent para-dioxane in high yield when passed over ZSM-5 or zeolite beta. Moreover, the conversion of diethylene glycol over ZSM-5 or zeolite beta is highly selective for 1,4 dioxane production. Both ZSM-23 and ZSM-48 exhibit the selectivity for diethylene glycol conversion to dioxane but not the same high yields. Formation of cyclic ether, para-dioxane, is favored over that of polyethylene glycol due the shape-selective nature of these zeolites.

The zeolite ZSM-5, its preparation and characteristic X-ray diffraction pattern are described in U.S. Pat. No. 3,702,886 and Re. 29,948. Zeolite beta, its preparation and its characteristic X-ray diffraction pattern are described in U.S. Pat. No. 3,308,069 and Re. 28,341. Each of said U.S. Pat. No. 3,702,886 and U.S. Pat. No. 3,308,069, Re. No. 29,948 and Re. No. 28,341 are incorporated by reference herein. ZSM-23, its preparation and its characteristic X-ray diffraction pattern is described in U.S. Pat. No. 4,076,842, the entirety of which is incorporated by reference herein. ZSM-48, its preparation and its characteristic X-ray diffraction pattern is described in U.S. Pat. No. 4,423,021, the entirety of which is incorporated by reference herein.

Data reported below show that both ZSM-5 and zeolite beta are ideally suited for this synthesis. Certain other zeolites of similar pore size tested below produce no appreciable amounts of dioxane. This implies that the additional internal volume provided in ZSM-5 or zeolite beta is necessary to accommodate the cyclic transition state in forming dioxane. The troglodytic nature of the acid sites in these zeolites accounts for the lack of any appreciable polymeric product. Accordingly, the reaction of diethylene glycol over either ZSM-5 or zeolite beta can be termed highly selective to dioxane product. Other large pore zeolites appear to age rapidly, since little dioxane was produced with these materials.

The zeolites, used in the process of the invention, can exhibit an alpha value of at least 1. The alpha value of the zeolite may be up to 1000 when used in the process of the invention. Generally, the alpha value will range from 1 to 300. The alpha value is a measure of zeolite acidity.

The alpha-test ($\alpha$-test) is an indication of the relative catalytic cracking activity of the catalyst compared to a standard catalyst. The value of $\alpha$ is the relative rate constant (rate of n-hexane conversion per unit volume of catalyst per unit time). It is based on the activity of highly active silica-alumina cracking catalyst taken as $\alpha = 1$.

The test for alpha value determination is described in a letter to the editor, entitled "Superactive Crystalline Alumino-Silicate Hydrocarbon Cracking Catalyst", by P. B. Weisz and J. N. Miale, *Journal of Catalysis*, Vol. 4, pp. 527–529 (August 1965) and in U.S. Pat. No. 3,355,078. The entire contents of both are expressly incorporated by reference herein. A procedure for determining the alpha value was more recently described in the *Journal of Catalysis*, Vol. VI, page 278–287, 1966, which is incorporated by reference herein.

The zeolites, used in accordance with the invention, may be used neat or supported on a matrix or binder inert to the selectivity of dioxane production during contact of diethylene glycol with ZSM-5 or zeolite beta, under intramolecular cyclization conditions. When the reaction is undertaken in the liquid phase, over a fixed catalyst bed, the reaction condition will include a liquid hourly space velocity (LHSV) of 0.1 to 200; temperature and pressure conditions will depend on the action of the catalyst temperatures of cyclization can range from 50° C. to 482° C. preferably from about 200° C. to 300° C. The pressure condition of cyclization can range from 0 to 400 psig. Presently, it is preferred to use high activity catalysts and low severity temperature and pressure conditions. The following examples illustrate the invention.

THE EXAMPLES

The following examples show that the zeolites ZSM-5 and zeolite beta are useful catalysts for the preparation of 1,4-dioxane from diethlylene glycol via ether cyclization. Example 4 demonstrates that these catalysts may also be useful for the conversion of ethylene glycol directly to dioxane by a two step process involving an intermediate diethylene glycol. In this latter example, however, the selectivity is lowered by competing dehydration to acetaldehyde, and its subsequent acetal formation. The selectivy might be improved by further catalyst modification (e.g. lowering catalyst activity, milder conditions, etc.). ZSM-35, which unlike ZSM-5 has no intersecting channels, gives little conversion presumably due to size constraints in accomodating the product-like transition state of ether cyclization. Neither Zeolon nor ZSM-4 give any appreciable dioxane product despite their large pore size. This may reflect very rapid aging of these materials either due to steam or other product formation. Subsequent to undertaking the experiments reported in the examples below, it was determined that both ZSM-23 and ZSM-48 exhibited the same selectivity, although not the same yields, in diethylene glycol cyclization of dioxane.

EXAMPLE 1

Diethylene glycol (Aldrich) was passed over ZSM-5 ($SiO_2/Al_2O_3 = 70$, $\alpha = 190$) at 200° C. (2 LHSV, 1 atm). Gas chromatographic analysis of the effluent revealed the following: diethylene glycol, 3.3%; dioxane, 86.9%;

other products (consisting of mainly acetaldehyde, ethylene glycol, and 2-methyl-1,3 dioxolane), 9.8%

EXAMPLE 2

Another sample of the above ZSM-5 catalyst was treated with a stream of diethylene glycol (200° C., 1 LHSV, 1 atm) with the following result: diethylene glycol, 0.0%; dioxane, 95.2%; other products (as above), 4.8%.

EXAMPLE 3

Example 2 was repeated with the following result: diethylene glycol, 0.0%; dioxane, 94.5%; other products, 5.5%.

EXAMPLE 4

A sample of ZSM-5 (identical to that described in example one) was treated with a stream of ethylene glycol (200° C., 1 LHSV, 1 atm). Gas chromatographic analysis of the effluent showed the following product distribution: ethylene glycol, 17.9%; diethylene glycol, 1.3%; dioxane, 60.1%; acetaldehyde, 6.4%; 2-methyl-1,3-dioxolane, 11.9%; other products, 2.4%.

EXAMPLE 5

A sample of zeolite beta (original $SiO_2/Al_2O_3=40$, steam calcined 2.5h, 538° C., 1 atm steam) was treated with a stream of diethylene glycol (200° C., 1 LHSV, 1 atm) with the following result: diethylene glycol, 0.3%; dioxane, 88.8%; triethylene glycol, 0.4%; other products (as above), 10.5%.

EXAMPLE 6

A sample of ZSM-35 ($\alpha=170$) was treated with a stream of diethylene glycol (200° C., 1 LHSV, 1 atm) with the following result: diethylene glycol, 96.9%; dioxane, 2.8%; other products, 0.4%.

EXAMPLE 7

A sample of Zeolon-H ($\alpha 21$) was treated with a stream of diethylene glycol (200° C., 1 LHSV, 1 atm) with the following result: diethylene glycol, 98.2%; dioxane 0.9%; other products, 0.1%.

EXAMPLE 8

A sample of Zeolon-H ($\alpha=443$-95 over 45 min TOS) was treated with a stream of diethylene glycol (200° C, 1 LHSV, 1 atm) with the following result: diethylene glycol, 97.1%; dioxane, 1.5%; other products (as above) 1.4%.

EXAMPLE 9

A sample of acid leached Zeolon-H ($SiO_2/Al_2O_3=98$; $\alpha=71$-64 over 45 min TOS) was treated with a stream of diethylene glycol (200° C., 1 LHSV, 1 atm) with the following result: diethylene glycol, 80%; dioxane, 17.3%; other products (as above), 2.7%.

EXAMPLE 10

A sample of ZSM-4 ($\alpha=42$) was treated with a stream of diethylene glycol (200° C., 1 LHSV, 1 atm) with the following result: diethylene glycol, 97.5%; dioxane, 1.7%; other products (as above), 0.8%.

The current invention provides a facile preparation of dioxane using a fixed bed process. Shape selectivity in zeolites like ZSM-5 or zeolite beta allows cyclization to the six membered ring ether, but prevents undesired polymerization. Thus, the advantages of this catalytic method far surpass existing homogeneous or heterogeneous dehydration processes, as well as those involving carcinogenic chlorinated intermediates (e.g. 2,2-dichlorodiethyl ether).

What is claimed is:

1. A process for preparing 1,4-dioxane comprising contacting diethylene glycol with a zeolite which is ZSM-5, ZSM-23, ZSM-48 or zeolite beta, under intramolecular cyclization conditions, wherein each of said zeolites is characterized by an alpha value of at least 1 and wherein the process is selective for dioxane production.

2. The process of claim 1, wherein diethylene glycol is in the liquid state and wherein the contacting is undertaken at a liquid hourly space velocity (LHSV) of 0.1 to 200.

3. The process of claim 1, wherein the intramolecular cyclization conditions include a temperature ranging from about 50° C. to 482° C. and a pressure ranging from 0 to 400 psig.

4. The process of claim 2, wherein the intramolecular cyclization conditions include a temperature ranging from 50° C. to about 482° C. and a pressure ranging from 0 to 400 psig.

5. The process of claim 1, wherein the catalyst is a fixed bed catalyst.

6. The process of claim 2, wherein the catalyst is a fixed bed catalyst.

7. The process of claim 3, wherein the catalyst is a fixed bed catalyst.

8. The process of claim 4, wherein the catalyst is a fixed bed catalyst.

9. The process of claim 1, wherein said alpha value is up to about 1000.

10. The process of claim 3, wherein said temperature ranges from 200° C. to 300° C.

11. The process of claim 2, wherein the cyclization conditions include a temperature ranging from 200° C. to 300° C.

12. The process of claim 1, wherein said zeolite is ZSM-5 or zeolite beta.

13. The process of claim 12, wherein said zeolite is ZSM-5 or zeolite beta.

* * * * *